(12) United States Patent  (10) Patent No.: US 7,391,892 B2
Gerwin  (45) Date of Patent: Jun. 24, 2008

(54) UNIVERSAL DIGITAL SUBTRACTION PHANTOM AND ANALYSIS SYSTEM AND METHOD

(75) Inventor: Paul J. Gerwin, Cincinnati, OH (US)

(73) Assignee: GE Medical Systems, Inc., Waukesha, WI (US)

( * ) Notice: Subject to any disclaimer, the term of this patent is extended or adjusted under 35 U.S.C. 154(b) by 874 days.

(21) Appl. No.: 10/723,937

(22) Filed: Nov. 26, 2003

(65) Prior Publication Data
US 2005/0111722 A1   May 26, 2005

(51) Int. Cl.
G06K 9/00 (2006.01)
(52) U.S. Cl. .................. 382/128; 382/296; 378/46
(58) Field of Classification Search ............ 382/128, 382/129, 130, 131, 132, 133, 154, 168, 181, 382/254, 255, 274, 276, 296, 100, 134, 189, 382/203, 232, 291, 305; 378/8, 207, 21, 378/46; 600/443, 431; 250/252.1
See application file for complete search history.

(56) References Cited

U.S. PATENT DOCUMENTS 6,224,257 B1* 5/2001 Launay et al. ............ 378/207
6,314,313 B1* 11/2001 Romeas et al. ............ 600/431
6,582,368 B2* 6/2003 Holdaway et al. .......... 600/443
6,845,142 B2* 1/2005 Ohishi ......................... 378/8
6,992,280 B2* 1/2006 White et al. ............. 250/252.1
7,125,166 B2* 10/2006 Eck et al. .................... 378/207

* cited by examiner

Primary Examiner—Seyed Azarian
(74) Attorney, Agent, or Firm—Fletcher Yoder (57) ABSTRACT

According to one embodiment, the present technique provides a phantom for testing imaging device. The exemplary phantom includes a first portion having groups of vessels, which are filled with a radiographically opaque substance (i.e., a contrast agent). The each group of vessels may extend from a central region of the first portion to the periphery of the central portion. The phantom may also include a second portion having a testing region. By way of example, the testing region may comprise a series of rings, each ring being configured to attenuate X-ray radiation differently. Adventurously, each ring may comprise materials configured to emulate different types and amounts of human tissue. For example, the exemplary phantom may include a ring, which emulates bone tissue, and a second ring, which emulates soft tissue. Moreover, each ring may be configured to emulate different amounts of tissue. That is to say, the certain rings in the phantom may include a first amount of a first material configured to emulate one kind of human tissue and a second amount of a second material configured to emulate a second kind of human tissue.

25 Claims, 5 Drawing Sheets

UNIVERSAL DIGITAL SUBTRACTION PHANTOM AND ANALYSIS SYSTEM AND METHOD

BACKGROUND OF THE INVENTION

The present technique relates to apparatus and methods for testing imaging devices. More particularly, the present technique relates to a phantom for testing imaging devices.

Medical imaging devices, such as X-ray systems, are omnipresent in modern medical facilities. Through the use of medical imaging devices, medical professionals, such as physicians, can produce detailed images of internal tissues, anatomies and organs of patients, thereby mitigating the need for invasive exploratory procedures and providing valuable tools for identifying and diagnosing disease and for verifying wellness.

Digital X-ray systems are becoming increasingly widespread for producing digital data that may be reconstructed into useful radiographic images. In traditional digital X-ray systems, a uniform beam of X-ray radiation is directed towards an object. As the beam passes through the object, materials of differing X-ray absorption and dispersion attenuate portions of the beam. Upon exiting the object, the attenuated X-ray beam impacts a detector, which measures the attenuation via photodiodes and transistors arranged in a matrix defining discrete picture elements or pixels of image data. By measuring this attenuation, the system may produce a radiographic image or projection of the object based upon the image data collected and processed. Advantageously, by analyzing the radiographic image, the physician may diagnose conditions of the patient.

Of particular note, digital subtraction angiography (DSA) procedures typically employ digital X-ray systems. To perform a DSA procedure, a medical professional may intravenously inject a contrast agent (e.g., a radiographically opaque substance, such as barium or iodine) into the patient to enhance the attenuation of the vasculature of the patient and provide desired contrast in the reconstructed X-ray image. That is, the medical professional may take a first image of the patient, without the contrast agent. This first image is generally known as a mask image. The medical professional may then intravenously inject the contrast agent into the patient. A second image of the patient is then taken. During typical DSA procedures, the patient must remain quite still to avoid artifacts and to improve the comparability of the resulting images. By subtracting the first image from the second image, primarily regions in which the newly injected contrast agent resides will remain visible in a difference or subtraction image. That is, the common elements of the two images are removed, leaving the newly injected contrast agent in the second image. Because the contrast agent flows within the circulatory system of the patient, the arteries and veins through which the contrast agent flows are highlighted.

Typically, the quality of the image produced by a digital X-ray system is defined by its contrast ability and by its resolution ability. In the medical industry, contrast ability refers to the extent to which the various different kinds of tissue within the body are displayed with respect to one another. That is, the discernability of one kind of tissue from another. Resolution, however, refers to the ability of the imaging device to reveal fine detail. That is, resolution typically refers to the ability to distinguish between small, closely spaced elements within the patient. By improving the contrast and resolution of a produced image, a physician, for example, may better diagnose a patient, because of the detail of the information provided by the image. Moreover, by gauging the abilities of the X-ray system, a physician may be able to determine whether the image is of sufficient detail to support a certain diagnosis. Higher resolution and contrast also aid in image enhancement processing on the collected image data in which features are filtered and otherwise clarified for analysis and viewing.

To improve the image produced and/or to gauge the capabilities of the imaging device, imaging devices are typically tested and/or calibrated. In certain instances, these testing and calibration procedures may employ phantoms. A phantom is generally an object of known physical characteristics that is placed in the system during test imaging sequences to determine how the system performs in one or more ways. Phantoms are typically used to measure system responses, adjust imaging parameters, qualify systems, calibrate systems, and so forth. The dimensions and composition of a phantom from which a test image is produced are known prior to the production of a test image. Thus, the test image of the phantom is compared with the known parameters of the phantom itself to reveal the accuracy and/or limitations of the imaging device. Accordingly, the imaging device may be recalibrated for maximum performance. Phantoms are typically designed based upon the physics of the particular type or modality of imaging system to be tested, and may be specifically designed for a particular type of image to be produced.

Typical phantoms, however, present a number of concerns. For example, traditional phantoms used to test for DSA procedures are relatively unwieldy items. That is, the technician may not be able to easily move such traditional phantoms from location to location. Moreover, traditional phantoms may not emulate human tissue ideally. For example, a traditional DSA phantom may be a substantially homogenous block of a clear plastic material. Accordingly, such construction may not accurately represent the diversity of tissue within the body. Moreover, in imaging procedures, such as DSA, inadvertent movement of the phantom may negatively impact the produced test image or images, i.e., the images used to generate the subtraction image.

Accordingly, there is a need for an improved technique for testing and gauging performance of imaging devices. Particularly, there is a need for a technique that reduces the difficulty and expense of servicing, repairing, calibrating and qualifying imaging devices, particularly those used for DSA imaging.

BRIEF DESCRIPTION OF THE INVENTION

The present invention provides techniques designed to respond to such needs. According to one embodiment, the present technique provides a phantom for use with an imaging device. By way of example, the phantom may be used to calibrate imaging devices, such as X-ray systems and systems employing X-ray radiation for imaging (such as tomosynthesis systems). The exemplary phantom includes a first portion rotatably coupled to a second portion. Within the first portion, a plurality groups of vessel-like regions comprise a generally radiographically opaque substance. Additionally, the vessel-like regions of each group may vary in size with respect to one another. The second portion may include first and second materials, which are radiographically similar to first and second kinds of human tissue, respectively. Because of the known composition of the phantom, the images produced by the phantom may be analyzed to determine the accuracy and/or limitations of the imaging device.

According to another embodiment, the present technique provides a method for testing an imaging device. The method includes producing a first image of a phantom, having a plurality of vessel-like regions containing a radiographically opaque substance, and a testing region which includes a first material radiographically similar to a first kind of human tissue and a second material radiographically similar to a second kind of human tissue. The first image may be an image of the phantom in a first configuration. The method also includes producing a second image of the phantom in a second configuration, wherein the second configuration alters the position of the vessel-like regions with respect to the first and second materials. Furthermore, the method includes producing a test image by subtracting the first image from the second image. By analyzing the subtraction image, a performance evaluation of the X-ray system may be developed. Advantageously, the performance evaluation may provide a standard against which performance of the same or other X-ray systems may be gauged.

DETAILED DESCRIPTION OF SPECIFIC EMBODIMENTS

Figure 1:
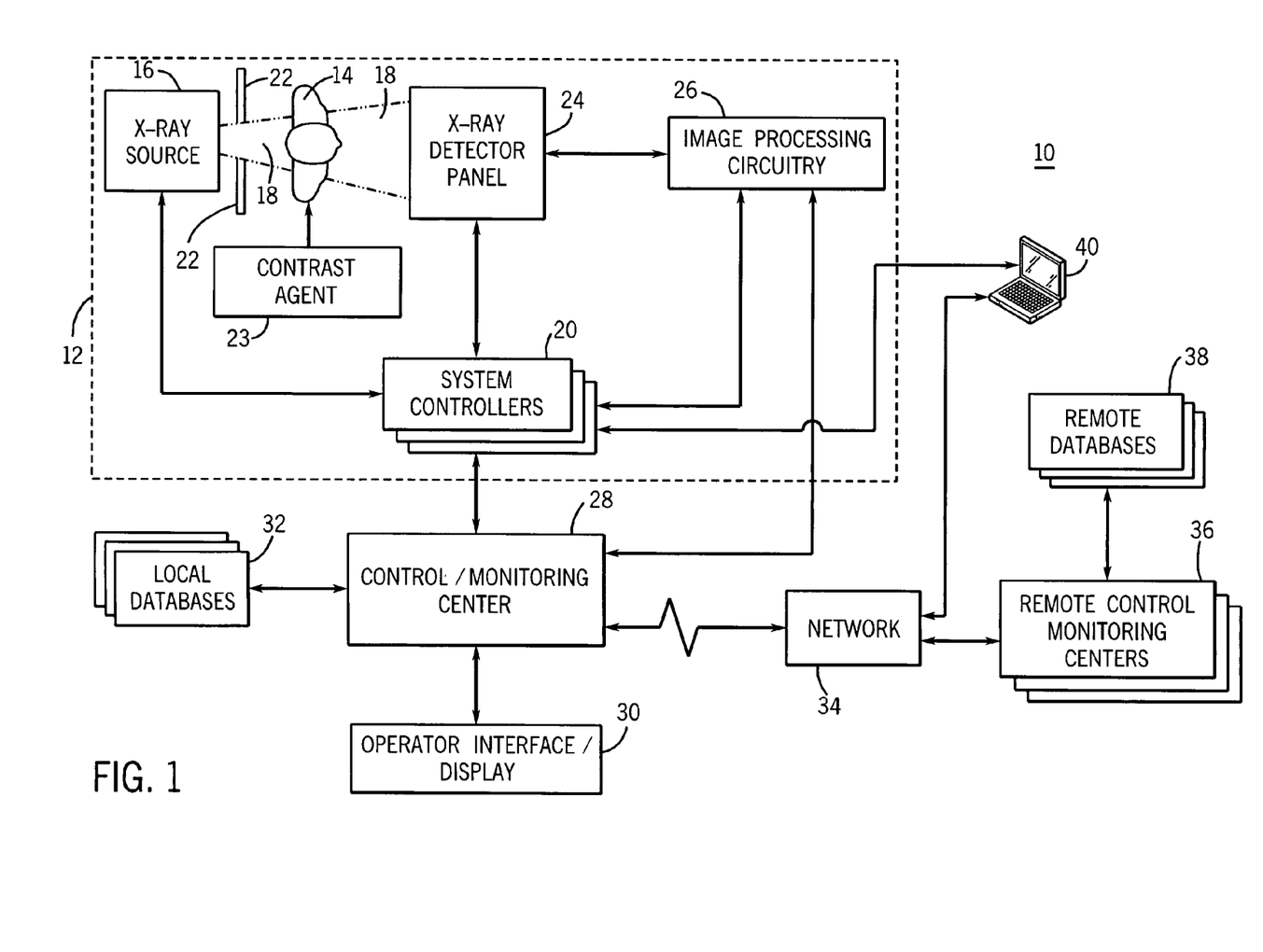
FIG. 1 is a diagrammatical representation of an exemplary X-ray imaging system designed to produce images of the type suitable for testing via the present technique.

Turning to the drawings, FIG. 1 illustrates an exemplary imaging network 10 with an X-ray system 12. More particularly, FIG. 1 illustrates a network for use with a digital X-ray system. By way of example, a digital fluoroscopy (DF) and/or digital angiography (DSA) technique may employ such digital X-ray systems, as discussed further below. However, it should be understood that the present technique is also applicable to other imaging modalities, such as computed tomography systems, X-ray mammography systems, and tomsynthesis systems, to name but a few types. Indeed, the present technique may benefit any number of imaging modalities in which images are produce by measuring differential X-ray attenuation.

When installed at a medical facility, a medical professional, such as a physician, radiologist, or device operator, may direct a patient 14 into a patient region of the X-ray system 12. Once the patient 14 is appropriately situated within the system, the operator may activate an X-ray source 16 to produce a beam 18 of X-ray radiation. One or more system controllers 20 may direct power to the X-ray source 16 from a power source and also may control operations of the X-ray source 16. By way of example, the system controllers 20 may include processor-based devices or programmable logic units (PLU). Moreover, the system controllers 20 also may coordinate operations of other components of the X-ray system 12 and network 10, as discussed further below. For automated control of the X-ray system 12, a computer program may provide commands and directions to the various system controllers 20. Additionally, the exemplary X-ray system 12 includes a collimator 22 that directs the beam 18 to a particular area of interest on the patient 14.

As the directed beam 18 of X-rays passes through the patient 14, various tissues within the patient attenuate the beam 18. For example, the tissue may absorb portions of the X-ray beam 18 and/or may dissipate some of the X-ray beam's energy. The attenuation of the beam 18 generally increases with the density and thickness of the object being imaged, which will depend upon the type and location of the tissues of the patient. Accordingly, the attenuation of the beam varies based upon the dimensions and characteristics of the materials traversed by the beam 18. That is to say, various kinds of human tissue will attenuate the X-ray beam 18 differently. For example, bone tissue will attenuate the beam significantly differently than lung tissue. Moreover, malignant cancerous tissue may attenuate the beam 18 differently than healthy non-cancerous tissue. By measuring the attenuation of the beam 18, the X-ray system 12 produces a radiographic image of the patient 14. Additionally, the insertion of a contrast agent into the patient, during certain procedures, may improve the readability and quality of the image produced.

In the exemplary X-ray system 12, an X-ray detector 24 measures the attenuation of the beam 18. By way of example, the X-ray detector 24 may consist of a scinitillator that converts X-ray photons received on the detector surface to lower energy (light) photons. An array of photodetectors, may convert the light photons to analog electrical signals, which are representative of the intensity of the beam 18 impacting a particular portion of the detector 24. Alternatively, a video camera may receive the light photons and convert the light photons into output signals. To convert these analog signals into an image, the X-ray detector 24 may transmit the analog signals to image processing circuitry 26 of the system. The image processing circuitry may include an analog-to-digital (A/D) converter, which converts the analog signals measured for pixel regions into a digital signal. Of course, the image processing circuitry may include other components that facilitate the production of a quality image from the X-ray system 12. Advantageously, system controllers 20, as discussed above, also may command and control the X-ray detector 24 and the image processing circuitry 26 and perform some or all of the signal processing required for reconstruction of images based upon the measured X-ray attenuation.

The image processing circuitry 26 may transmit the produced image data, raw, partially or fully processed, to a control and monitoring center 28, which may command and monitor the various system controllers 20 in the X-ray system. The control and monitoring center 28 may communicate with an operator interface/display 30. Advantageously, the operator interface may display the produced image to the medical professional for diagnostic purposes, or at least to verify that the desired regions and images have been produced during an imaging session. Moreover, the operator interface may receive inputs from the operator and may transmit such inputs to the X-ray system 12. The control and monitoring center 28 may communicate with local databases 32 for storing the images produced, for example.

In many instances, the X-ray system 12 may communicate with remote locations and devices via a network 34, such as a Local Area Network (LAN), a Server Area Network (SAN), a Metropolitan Area Network (MAN), a Wide Area Network (WAN), a Virtual Private Network (VPN), the Internet, or any other suitable kind of network. Communications over the network 34 may be conducted via any number of communications schemes and protocols, such as Global Standard for Mobile (GSM), Time Division for Multiple Access (TDMA), Code Division Multiple Access (CDMA), Frequency Division Multiple Access (FDMA), radio frequencies (RF), or any other suitable communications techniques. By way of example, the imaging network 10 may include remote monitoring centers 36, which may receive operation data and imaging data from the X-ray system 12 via the network 34. Advantageously, the remote monitoring centers 36, communicating via the network 34, may improve the image data quality as well as monitor and adjust the operating parameters remotely.

The network also 34 may facilitate access to remote databases 38. Advantageously, the remote databases 38 may store large volumes of image data and operating data from a wide variety of sources coupled to the network. That is, data from multiple X-ray systems 12 and patients 14 may be stored at a central location. Indeed, image or operating data may be accessed by user interfaces 30 at locations remote from the X-ray system 12 that produced the data.

In certain instances, a field technician may wish to access data or alter operating parameters related to the X-ray system 12. Accordingly, a field unit 40, such as a laptop computer or hand-held device, may communicate with the system controllers 20. To improve portability, the field unit 40 may be configured to communicate with the system controllers 20 via a wireless protocol, such as IEEE 802.11(b), Bluetooth, or RF communications. Advantageously, the field technician, via the field unit 40, may monitor operations of the X-ray system 12 and provide system adjustments in response to improve the quality of the images produced. Furthermore, the field technician may remotely access data regarding the operations of the imaging device, for purposes of testing and calibration. Of course, the field unit 40 also may communicate with the X-ray system 12, the databases, and control centers via the network 34.

The quality of the X-ray system 12 may be judged by the contrast and resolution of the image produced. Contrast refers to the extent to which the various kinds of tissues and features of interest are distinguishable on the image produced. For example, the various tissue structures may produce various shades of gray, as determined in part by the inherent properties of the different kinds of tissue, such as thickness, density (e.g., lung tissue vs. muscle tissue), and chemical composition (e.g., bone tissue vs. soft tissue). Resolution, however, refers to the ability of the X-ray system 12 in revealing fine detail. That is, resolution usually refers to the ability to distinguish between small, high-contrast objects that lie close to one another. As discussed further below, the contrast and resolution of an image produced by the X-ray system 12 may be analyzed to calibrate and/or grade the X-ray system 12.

However, if the attenuation is too great, the image processing circuitry 26 and/or the detector 24 may not properly distinguish between various tissue types. That is, the attenuation of the beam 18 is outside the detectable dynamic range of the X-ray system 12. Similarly, if the too little attenuation of the beam occurs, the imaging processing circuitry may again fail to distinguish between the various types of tissue in the patient, an event referred to in the pertinent art as "wash out."

Figure 2:
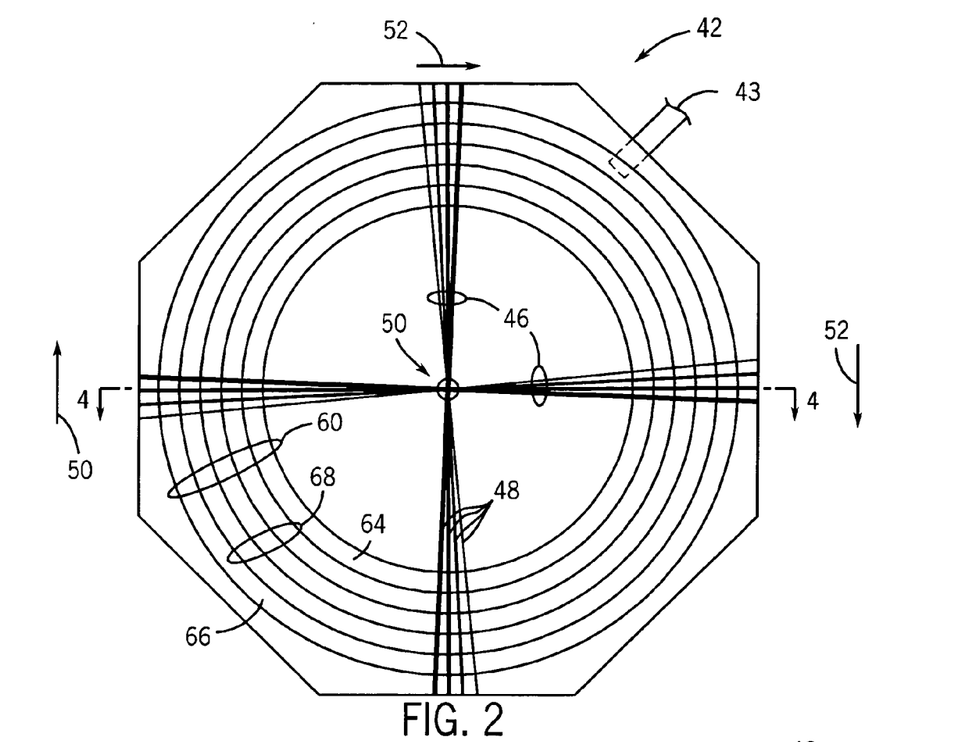
FIG. 2 is a top view of an exemplary phantom having features in accordance with aspects of the present technique.
Figure 3:
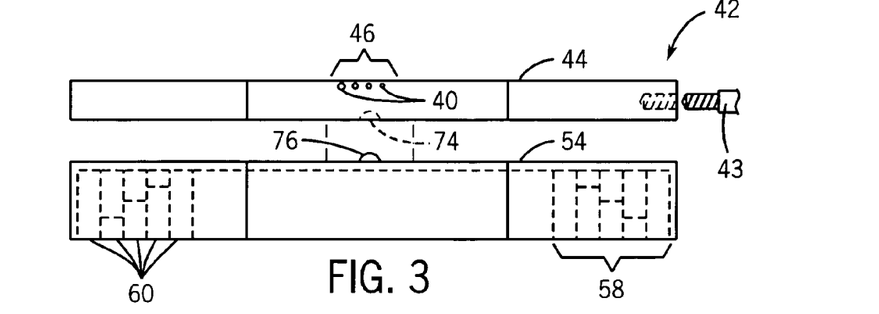
FIG. 3 is a side view of the exemplary phantom of FIG. 2, wherein the upper and lower portions are shown in an exploded arrangement with respect to one another.
Figure 4:
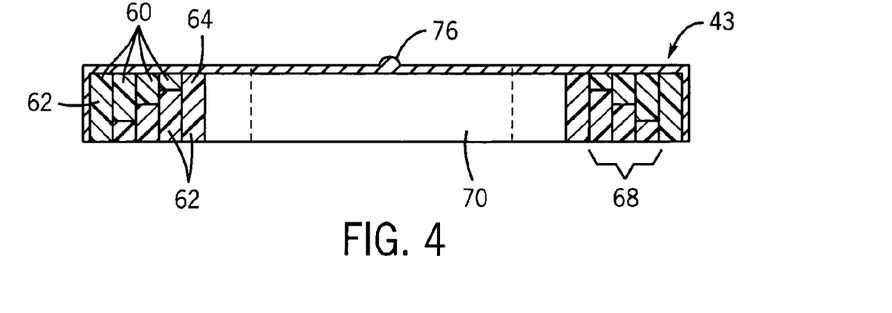
FIG. 4 is a cross-sectional illustration of the phantom of FIG. 2 along line 4-4, showing only the lower portion of the phantom in accordance with aspects of the present technique.

To test and/or calibrate an X-ray system 12, a technician may employ a phantom 42, as illustrated in FIGS. 2-4. Because the composition of the phantom is known, a comparison of the produced image with the known parameters of the phantom may gauge the performance of the X-ray system 12, as discussed further below. The exemplary phantom 42 is a generally polygonal or circular shaped instrument, which may be sized for portability. For example, the phantom 42 may be part of a tool-kit that a technician transports manually from one X-ray system 12 location to another. Accordingly, the phantom 42 may comprise components formed of relatively lightweight materials, such as plastic or aluminum, or a combination of fairly lightweight materials.

The exemplary phantom 42 has an upper portion 44 (with respect to the orientation of FIG. 3) that carries one or more groups 46 of vessel-like regions. Each group 46 comprises a number of vessel-like regions 48 that extend radially outward from a central region 50 of the upper portion 44. Each vessel-like region 48 comprises a relatively radiographically opaque substance (i.e., contrast agent), such as iodine or barium, or a material that mimics such substances for imaging purposes. Accordingly, for purposes of testing an X-ray system 12 (see FIG. 1), the vessel-like regions 48 may represent various arteries and veins of a patient circulatory system. Moreover, to better represent an actual circulatory system, each vessel-like region 48 within each group 46 may vary in size. For example, the vessel-like regions 48 of each group 46 may have cross-sectional areas or dimensions that vary with respect to one another. For consistency, however, the vessel-like regions 48 of each group may be arranged from smallest dimensioned region to largest in a clockwise orientation, as represented by directional arrows 52 (see FIG. 2). Moreover, the corresponding vessel-like regions 48 of the different groups 46 may be substantially identical in size. That is to say, the smallest vessel-like region of each group may be substantially identical in size, the largest vessel-like region 48 of the various groups may also be substantially identical in size, and so forth. Furthermore, to better represent actual testing environments, each group 46 in the phantom 42 may comprise different concentrations of the radiographically opaque substance. As one example, the most concentrated group may have an iodine concentration of 75 mg/cc, whereas the least concentrated group may have an iodine concentration of 25 mg/cc. Again, the regions may comprise various materials that radiologically mimic the actual contrast agents employed in imaging a subject patient.

The exemplary phantom also includes a lower portion 54 (with respect to the orientation of FIG. 3) that is rotatably coupled to the upper portion 44. Advantageously, the phantom 42 may include an arm 56 removably coupled to the upper portion or the lower portion to provide leverage for rotating the portions of the phantom 42 with respect to one another. Moreover, the arm 54 may facilitate rotation of the portions with respect to one another without significant exposure to an imaging bay, in which X-ray radiation will typically be released during imaging. The arm also permits the field service technician to access and manipulate the phantom easily during use. The lower portion 54 includes a testing region 58. The testing region 58 may comprise concentrically arranged test rings 60 of attenuation materials 62 (see FIG. 4) that are radiographically similar to human tissue. By way of example, the attenuation materials 62 may include epoxy compounds that are radiographically similar to various kinds of human tissue, e.g., bone tissue, soft tissue, or cancerous tissue. It should be noted, however, that any number of tissues types may be represented by the various attenuation materials 62. Indeed, for the purposes of testing the X-ray system, the attenuation materials 62 within the testing region 58 may correspond with the diversity of human tissue within a patient anticipated during an actual examination.

As illustrated best by FIG. 4, in which only the lower portion 54 is shown in this cross-sectional view, the each test ring 60 may include varying amounts of attenuation material 62. In the exemplary phantom 42, the innermost ring 64 may comprise primarily a first attenuating material having certain radiographic characteristics, and the outermost ring 66 may comprise primarily a second attenuation material having radiographic characteristics different than the first attenuation material. By way of the example, the first attenuating material (i.e., the attenuating material in the innermost ring 64) may attenuate X-ray beams in a manner similar to soft tissue, whereas, the outermost ring 66 may attenuate the X-ray beam in a manner similar to bone tissue. The intermediate test rings 68 may comprise strata having various amounts of the first and second attenuation materials 62. Again, by way of example, the strata in the intermediate rings 68 may be arranged such that the outermost intermediate rings comprise more of the second attenuation material, which attenuates the beam 18 similar to bone tissue, for example, whereas, the innermost intermediate rings may comprise more of the first attenuation material, which attenuates the X-ray beam 18 similar to soft tissue, for example. Accordingly, for consistency and testing purposes, the test rings 60 in the exemplary phantom are arranged such that the rings that attenuate the beam 18 (see FIG. 1) the most are located towards the outer periphery of the phantom 42.

The lower portion 54 also may include a calibration region 70. The calibration region 70 may comprise a composite material with a neutral density. By way of example, the calibration region may comprise a material with a radiographic density of water, or may comprise certain specific materials, such as copper. Advantageously, the calibration region 70 may facilitate an automatic system selection technique for stabilizing the X-ray system 12 prior to testing. As one example, the automatic system selection technique may stabilize the X-ray source 16 (see FIG. 1) to a 70 peak kilovoltage (kVp) level.

When the upper and lower portions of the phantom are properly coupled to one another, the vessel-like regions 48 of the upper portion 44 overlap the test rings 60 of the lower portion 54, as best represented by FIG. 2. Accordingly, the phantom 42 may emulate practical scenarios that the X-ray system 12 may encounter. For example, in the exemplary phantom 42, each vessel-like region 48 of each group 46 overlaps each testing ring, i.e., the innermost, outermost, and intermediate testing rings. As discussed further below, by analyzing the images produced via the phantom 42, qualities of the X-ray system 12 (see FIG. 1) may be determined. Advantageously, the upper and lower portions 44 and 54 may include corresponding notch 74 and detent structures 76 to assist in the alignment and coupling of the two portions.

Advantageously, the exemplary phantom 42 allows for the testing of at least four discrete variables with respect to an imaging device: These include the impact of vessel size; the impact of varying material composition; the impact of material quantities; and the impact of contrast agent concentration on image contrast and resolution, in different combinations of overlying vessels and tissues. Indeed, via one tool, each of the foregoing factors may be tested and evaluated separately and in combination.

Figure 5:
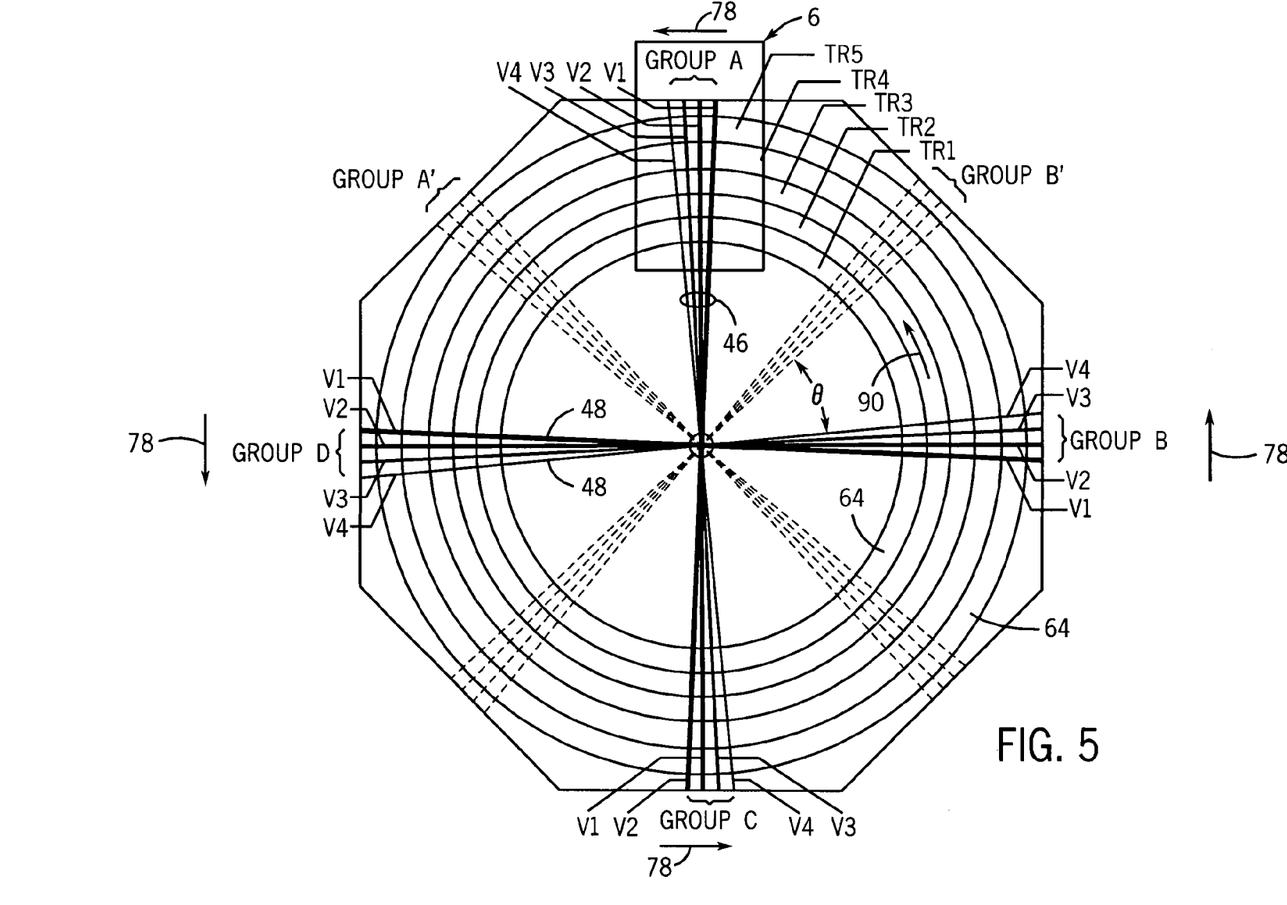
FIG. 5 is a representation of an exemplary identification system for various components of the phantom of FIG. 2, in accordance with aspects of the present technique.
Figure 7:
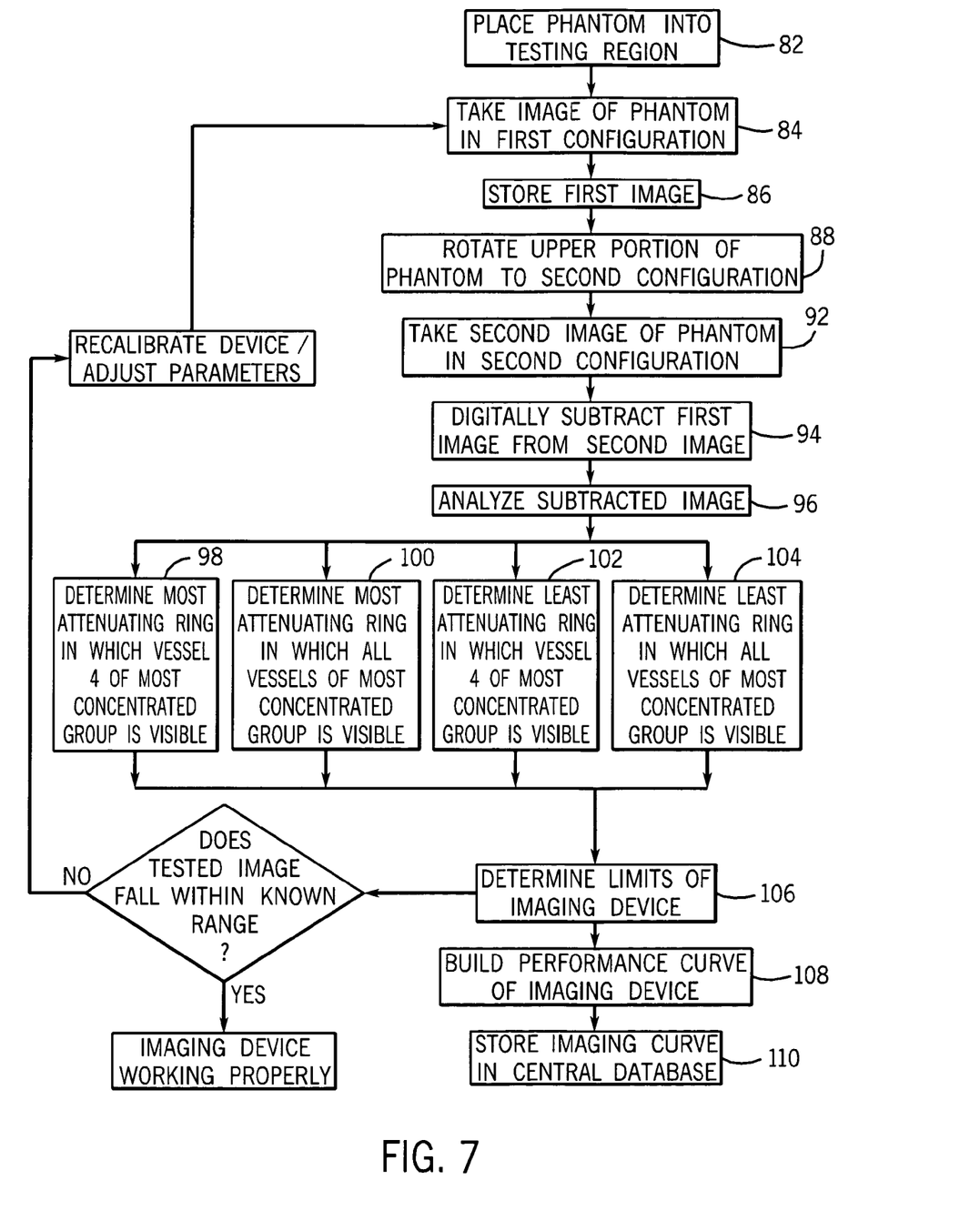
FIG. 7 is a flow chart representing steps in an exemplary process in accordance with aspect of the represent technique.

As one particularly useful application, the exemplary phantom 42 may be employed during a DSA X-ray system test, particulars of which are discussed in further detail below with respect to FIG. 7. Prior to addressing FIG. 7, FIG. 5 illustrates an exemplary identification scheme for the exemplary phantom for use during a DSA test. The exemplary phantom 42 has four groups 46 (Groups A to D) of four vessel-like regions 48 (V1 to V4). The Group A has the highest concentration of iodine (e.g., 75 mg/cc) and Group D has the lowest concentration of iodine (e.g., 25 mm/cc). The iodine concentration of Groups B and C appropriately fall within this exemplary range, i.e., Group B has a higher iodine concentration than group C. Accordingly, each vessel-like region 48 in each group 46 comprises equivalent concentrations of iodine or of a substance that mimics iodine. Each group 46 contains four vessel-like regions 48 that are labeled V1 to V4 in a counter clockwise orientation, as represented by directional arrow 78. In each group 46, the vessel-like regions 48 are arranged such that V1 is the largest (i.e., widest) region and V4 is the smallest (i.e. narrowest) region. In the exemplary phantom 42, each of the vessel-like regions 48 overlaps each the test rings 60. The test rings are arranged such that the innermost ring 64 (TR1) attenuates the beam 18 less than the outermost ring 66 (TR5). Accordingly, the attenuation of the beam 18 increases as towards the outer perimeter of the phantom 42. That is, attenuation of the beam increases stepping from TR1 to TR5.

Figure 6:
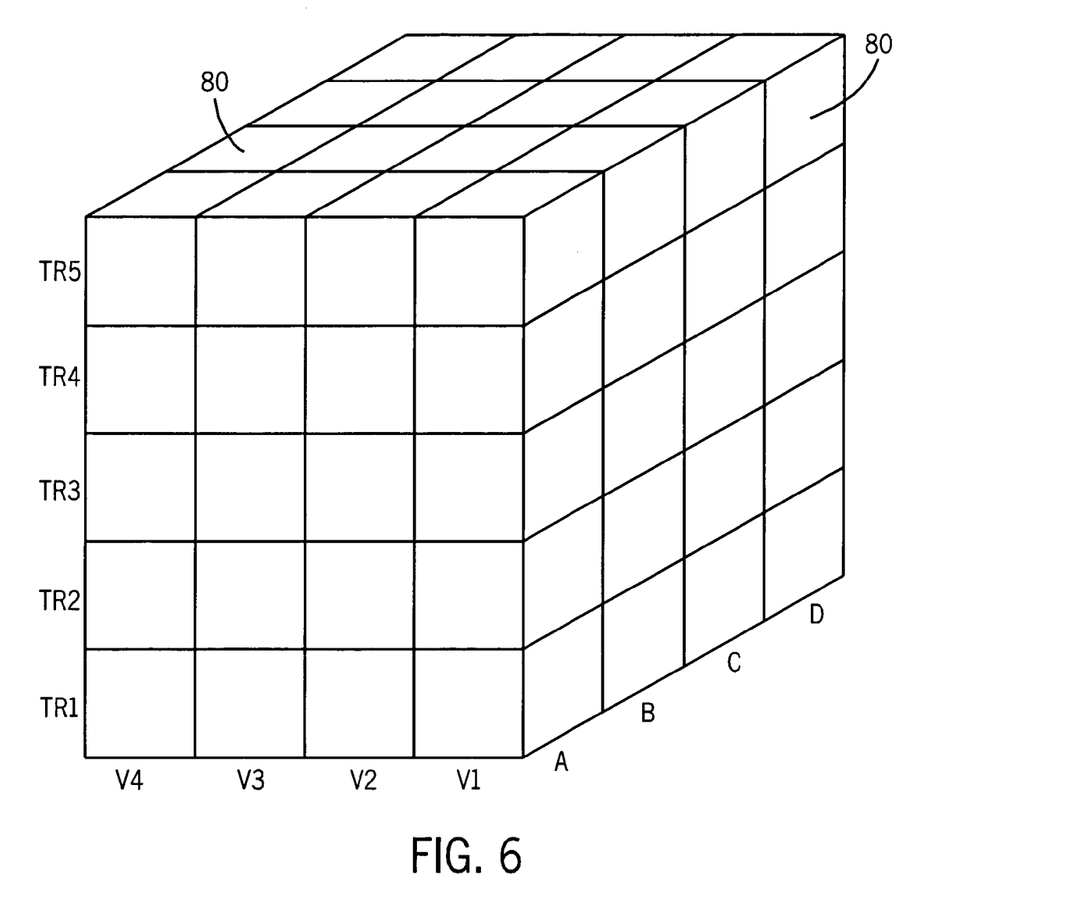
FIG. 6 represents an exemplary coordinate system for identifying regions of the phantom of FIG. 2, in accordance with aspects of the present technique.

In accordance with the exemplary identification scheme discussed precedingly, a coordinate system for the overlap of each vessel-like region 48 and test ring 60 may be employed, as illustrated in FIG. 6. As illustrated, the vessel-like regions are represented on the horizontal axis, the test rings are represented on the vertical axis, and the groups are represented on the diagonal axis. In the exemplary coordinate system, each cell 80 represents a unique combination of an overlapping vessel-like region 48 of a particular vessel group 46 and with a particular test ring 60. Accordingly, the exemplary coordinate system may identify a particular section of the image. For example, the coordinates (V4, TR1, A) identify the cell 80, or overlap between the smallest vessel-like region of Group A and the test ring configured to attenuate the beam 18 the least. Of course, other identifications or coordinate schemes may be envisaged. Indeed, the present coordinate scheme is presented primarily for the purpose of explanation.

FIG. 7 illustrates an exemplary process for testing and calibrating an exemplary DSA X-ray system 12. The exemplary process includes placing the phantom 42 into the X-ray system 12, as represented by block 82. As discussed above, the exemplary phantom 42 may radiographically emulate patient tissue for the purposes of testing. An operator may activate the X-ray source 16, thereby directing a beam of X-ray radiation through the phantom 42. The detector panel 24 may receive the attenuated beam 18, from which the imaging processing circuitry 26 may produce an image of the phantom in the first configuration. Block 84 represents these steps in the exemplary process. The network 10 may then store the image at an appropriate location, such as within the processing circuitry, or within the remote and local databases 38 and 32. Block 86 represents this step in the exemplary process. The phantom 42, which is located in the X-ray system 12, may be rotated into a second configuration, as represented by block 88. By way of example, the upper portion 44 may be rotated by an angle θ (see FIG. 5) with respect to the lower portion 54, as represented by directional arrow 90 (see FIG. 5). In FIG. 5, the vessel-like regions 48 shown in dashed lines illustrate the groups 46 repositioned in the second configuration. The X-ray source 16 may be activated, and the detector 24 and the image processing circuitry 26 may cooperate to produce an image of the phantom 42 in the second configuration, as represented by block 92. Subsequently, to produce a subtraction image, the processing circuitry may recall the first image and subtract the first image from the second image, as represented by block 94.

The subtraction image may then be analyzed to determine the limits or performance of the X-ray system 12, as represented by block 96. In the exemplary phantom 42, vessel-like regions V4 of each vessel group 46 have the smallest spatial dimension. Accordingly, to find the upper limit of the resolving and contrasting ability (i.e., the point at which the attenuation is too great for the X-ray system 12 to resolve and/or contrast the object), the tester may locate the cell 80 on the subtraction image in which the smallest vessel-like region (i.e., V4) of the most concentrated (i.e. radiographically opaque) group (e.g., Group A) is visible in the ring containing the attenuation material that attenuates the beam 18 the most (i.e., TR5). For example, a tester analyzing the image may begin with the cell 80 with the coordinates (V4, TR5, A). If no vessel image is found, or if the resolution or contrast is inadequate, then the tester may move to the next lowest test ring, that is the cell 80 with coordinates (V4, TR2, A). If no portion of V4 is adequately discernible in the image, the tester may move to the next largest vessel, in this case V3. That is, the tester may move to the cell 80 with coordinates (V3, TR5, A). This procedure may be repeated until the image of the vessel is found and resolution and contrast are satisfactory. This process is represented by block 98.

The subtraction image may also be analyzed to determine the low contrast resolving ability of the system. To accomplish this, the tester may locate the test ring that attenuates the beam the most and in which all of the vessel-like regions of the group with the highest concentration of contrast agent are visible in the image. For example, the tester may analyze the image of Group A and determine that all of the vessel-like regions of Group A are not visible in test rings TR4 and TR5 and are first visible in test ring TR3. That is, the cells 80 represented by coordinates (V4, TR3,A) to (V1, TR3,A). This step in the process is represented by block 100.

Additionally, it may be advantageous to determine the lower limit of resolving and contrast ability (i.e., the point at which the attenuation is too small for the X-ray system 12 to resolve or contrast the object). Accordingly, to find the lower limit of the resolving and contrasting ability, the tester may locate the cell 80 on the subtracted image in which the smallest vessel-like region (i.e., V4) of the most concentrated vessel group (e.g., Group A) is visible in test ring that attenuates the beam 18 the least (e.g., TR1). For example, a tester analyzing the image may begin with the cell 80 with the coordinates (V4, TR1, A). If no vessel image is found, or if the resolution or contrast is inadequate, then the tester may move to the next highest test ring, that is the cell 80 with coordinates (V4, TR2, A). If no V4 vessel is present in the image, of if the resolution or contrast is still inadequate, then technician may move to the next largest vessel, in this case V3. That is, the technician may move to the cell 80 with coordinates (V3, TR1, A). This procedure may be repeated until the image of the smallest vessel-like region is visible with satisfactory contrast and resolution. This process is represented by block 102.

The subtraction image may also be analyzed to determine the contrast resolving ability in the lowest attenuation range. To accomplish this, the tester may locate the test ring that attenuates the beam the least, and in which all of the vessel-like regions of the group with the highest concentration of contrast agent are visible in the image. For example, the tester may analyze the image of Group A and determine that all of the vessel-like regions of Group A are not visible or adequately discernible in test rings TR2 and are first visible in test ring TR1. This step in the process is represented by block 104.

Via analysis of the phantom, as exemplified above, the limits of the X-ray system 12 may be determined, that is, the ability of the X-ray system 12 to resolve and contrast materials that attenuate the beam 18 too much or too little to produce a desirable image. This step is represented by block 106. The foregoing process may be conducted for both inverted and non-inverted imaging. One or the other of such techniques may be desired by certain observers, with inverted imaging generally providing a presentation similar to conventional film-based X-ray images.

Advantageously, the foregoing determined values may define a performance evaluation or curve for the X-ray system 12. By reviewing the performance curve, the quality of the image produced and the X-ray system may be determined. For example, by reviewing the performance curve, a physician may determine that the given X-ray system 12 would not provide the resolution or contrast ability to support a medical diagnosis. Moreover, the performance curve from similar X-ray systems may be compiled to determine a sample or standard performance curve. For example, the remote control and monitoring center may receive performance data from X-ray systems 12 located at various medical facilities via the network 34. Once received, the performance data may be complied, via various forms of statistical analysis, to produce a standardized or ideal performance curve for the given type of X-ray system 12. This standardized performance curve may then be stored remotely in the remote databases 38 or locally in the local databases 32. Blocks 108 and 110 represent these steps in the process. It should be noted that the performance curve may be stored and accessed at any number of locations because of the connectivity of the network.

The performance curve, whether of the X-ray system itself or of similar X-ray systems 12, may indicate whether the tested X-ray system 12 is operating properly. For example, if a subtraction test image of the exemplary phantom indicates that the highest level of resolving and contrast ability in the most attenuating materials occurs in cell (V4, TR3, B) of the image and the performance curve indicates that the X-ray system is capable of resolving and contrasting the image in cell 80(V4, TR2, B), then the tested X-ray system 12 may not be operating properly. Block 112 represents this step in the exemplary process. If so, then the X-ray system 12 may be recalibrated and adjusted to correct for any possible errors, as represented by block 114. Once recalibrated, the system may be retested and the process may be repeated until a satisfactory test image is obtained, as represented by block 116.

While the invention may be susceptible to various modifications and alternative forms, specific embodiments have been shown by way of example in the drawings and have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. A phantom for use with an imaging device, comprising:
a first portion including at least one group of vessel-like regions having a radiographically opaque quality, wherein the at least one group of vessel-like regions includes at least first and second vessel-like regions such that the first vessel-like region is larger than the second vessel-like region; and
a second portion coupled to the first portion and rotatable with respect to the first portion, the second portion having a testing region of material radiographically similar to human tissue;

wherein the phantom comprises a plurality of groups of vessel-like regions, wherein a first group of vessel-like regions comprises a first concentration of a radiographically opaque material and a second group of vessel-like regions comprises a second concentration of a radiographically opaque material.

2. The phantom as recited in claim 1, wherein the phantom is manually portable.

3. The phantom as recited in claim 1, wherein the testing region includes a first material radiographically similar to a first kind of human tissue and a second material radiographically similar to a second kind of human tissue.

4. The phantom as recited in claim 3, wherein the first and second materials are located adjacent to one another.

5. The phantom as recited in claim 1, wherein the radiographically opaque quality is a radio-opacity equivalent to iodine.

6. The phantom as recited in claim 1, wherein the radiographically opaque quality is a radio-opacity equivalent to barium.

7. The phantom as recited in claim 1, comprising an arm for rotating the first portion with respect to the second portion.

8. A phantom for use with an imaging device, comprising:
a first portion having at least one group of vessel-like regions extending from a first portion central region and towards a periphery of the first portion, wherein the at least one group of vessel-like regions has a level of a radiographically opaque quality; and
a second portion coupleable to the first portion and having a first testing region and a second testing region arranged circumferentially with respect to one another, wherein the first testing region includes a first attenuation material radiographically similar to a first type of human tissue and the second testing region includes a second attenuation material radiographically similar to a second type of human tissue, the first testing region being configured to attenuate X-ray radiation more than the second testing region.

9. The phantom as recited in claim 8, wherein the first testing region is located towards the periphery of the first portion and the second portion is located towards the first portion central region.

10. The phantom as recited in claim 8, comprising a calibrating region.

11. The phantom as recited in claim 8, wherein the calibrating region includes at least one of copper and water.

12. The phantom as recited in claim 8, wherein the first and second portions are couplable to one another such that the at least one group of vessel-like regions overlaps the plurality of testing regions.

13. A phantom for use with an imaging device, comprising:
a first portion having at least first and second vessel-like regions each having a radiographically opaque quality, wherein the first vessel like region is larger than the second vessel like region; and
a second portion coupled to the first portion and rotatable with respect to the first portion and including a first material radiographically similar to a first kind of human tissue located adjacent to a second material radiographically similar to a second kind of human tissue;
wherein the phantom comprises a plurality of groups of vessel-like regions, wherein a first group of vessel-like regions comprises a first concentration of a radiographically opaque material and a second group of vessel-like regions comprises a second concentration of a radiographically opaque material.

14. The phantom as recited in claim 13, wherein the first kind of human tissue is bone tissue.

15. The phantom as recited in claim 13, wherein the first kind of human tissue has a density greater than the second kind of human tissue.

16. The phantom as recited in claim 13, wherein the first and second materials comprise an epoxy.

17. A method for testing an imaging device, comprising:
producing a first radiographic image of a phantom comprising a first portion and a second portion rotatable with respect to the first portion and having a plurality of vessel-like regions having a radiographically opaque quality extending radially from a central region of the phantom and a testing region including a first material radiographically similar to a first kind of human tissue a second material radiographically similar to a second kind of human tissue, wherein the phantom is in a first configuration for producing the first radiographic image; and
producing a second radiographic image of the phantom in a second configuration, wherein the vessel-like regions in the second configuration are repositioned with respect to the position of the vessel-like regions in the first configuration by rotation of the first portion of the phantom with respect to the second portion of the phantom; and
producing a test image by subtracting the first image from the second image.

18. The method as recited in claim 17, wherein producing comprises producing a digital X-ray image.

19. The method as recited in claim 17, comprising stabilizing the imaging device via a calibration region located in the phantom.

20. A system for testing an imaging device, comprising:
means for producing a first radiographic image of a phantom comprising a first portion and a second portion rotatable with respect to the first portion and having a plurality of vessel-like regions having a radiographically opaque quality extending radially from a central region of the phantom and a testing region including a first material radio graphically similar to a first kind of human tissue a second material radiographically similar to a second kind of human tissue, wherein the phantom is in a first configuration for producing the first radiographic image; and
means for producing a second radiographic image of the phantom in a second configuration, wherein the vessel-like regions in the second configuration are repositioned with respect to the position of the vessels in the first configuration by rotation of the first portion of the phantom with respect to the second portion of the phantom; and
means for producing a test image by subtracting the first image from the second image.

21. A method for testing an imaging device, comprising:
providing a subtracted image of a phantom having a plurality of testing regions each region being configured to attenuate X-ray radiation at varying degrees arranged circumferentially with respect to one another and at least one group of vessel-like regions having a radiologically opaque quality overlappingly arranged with respect to the circumferentially arranged testing regions; and
analyzing the subtracted image to determine the smallest vessel-like region of the vessel group of vessel-like regions visible in the test region having the highest degree of attenuation to determine an upper limit of the imaging device.

22. The method as recited in claim 21, comprising:

analyzing the subtracted image to determine the smallest vessel-like region of the group of vessel-like regions visible in the test region having the lowest degree of attenuation to determine a lower limit of the imaging device.

23. The method as recited in claim 22, comprising developing a performance standard for the imaging device based on the upper and lower limits of the imaging device.

24. The method as recited in claim 23, comprising calibrating the imaging device based upon the performance standard and a pre-determined ideal performance standard.

25. A testing system for an imaging device, comprising:

means for providing a subtracted image of a phantom having a plurality of testing regions each region being configured to attenuate X-ray radiation at varying degrees arranged circumferentially with respect to one another and at least one group of vessel-like regions having a radiologically opaque quality overlappingly arranged with respect to the circumferentially arranged testing regions; and means for analyzing the subtracted image to determine the smallest vessel-like region of the group of vessel-like regions visible in the test region having the highest degree of attenuation to determine an upper limit of the imaging device.

* * * * *